United States Patent [19]
Johnson

[11] Patent Number: 5,226,875
[45] Date of Patent: Jul. 13, 1993

[54] ATHLETIC FOOTWEAR WITH INTEGRAL ANKLE SUPPORT

[76] Inventor: James Johnson, 1702 S. University Ave., P.O. Box 6001, Fargo, N. Dak. 58108

[21] Appl. No.: 801,271
[22] Filed: Dec. 2, 1991
[51] Int. Cl.⁵ .............................................. A61F 3/00
[52] U.S. Cl. .......................................... 602/27; 36/89; 36/55; 36/120
[58] Field of Search .................... 36/89, 90, 88, 48, 57; 602/27; 128/80 H

[56] References Cited

U.S. PATENT DOCUMENTS

| | | | |
|---|---|---|---|
| 3,327,410 | 5/1965 | Park, Sr. et al. | 36/89 |
| 3,977,098 | 8/1976 | Chalmers | 36/89 |
| 4,280,489 | 7/1981 | Johnson, Jr. | 602/27 |
| 4,726,126 | 2/1988 | Bernhard | 36/89 |
| 4,771,768 | 9/1988 | Crispin | 602/27 X |

Primary Examiner—Richard J. Apley
Assistant Examiner—Beverly A. Meindl
Attorney, Agent, or Firm—Douglas L. Tschida

[57] ABSTRACT

Athletic footwear including a pair of resilient ankle braces which are supported to the sole, inner lining and a separately bound calf support collar of an athletic shoe. The braces are configured of a deformable polymer and include apertures shaped to accommodate protruding ankle bones. Curved lower ends of each brace mount to the heel region of the sole. Formed pockets or restraint means support the braces to the shoe liner. A separately mounted, cushioned collar restrains the upper brace end to the calf. In other constructions, one or more cushioned brace portions may be supported between the shoe and foot. In still another construction, a two-piece, hinged polymer brace is considered.

19 Claims, 8 Drawing Sheets

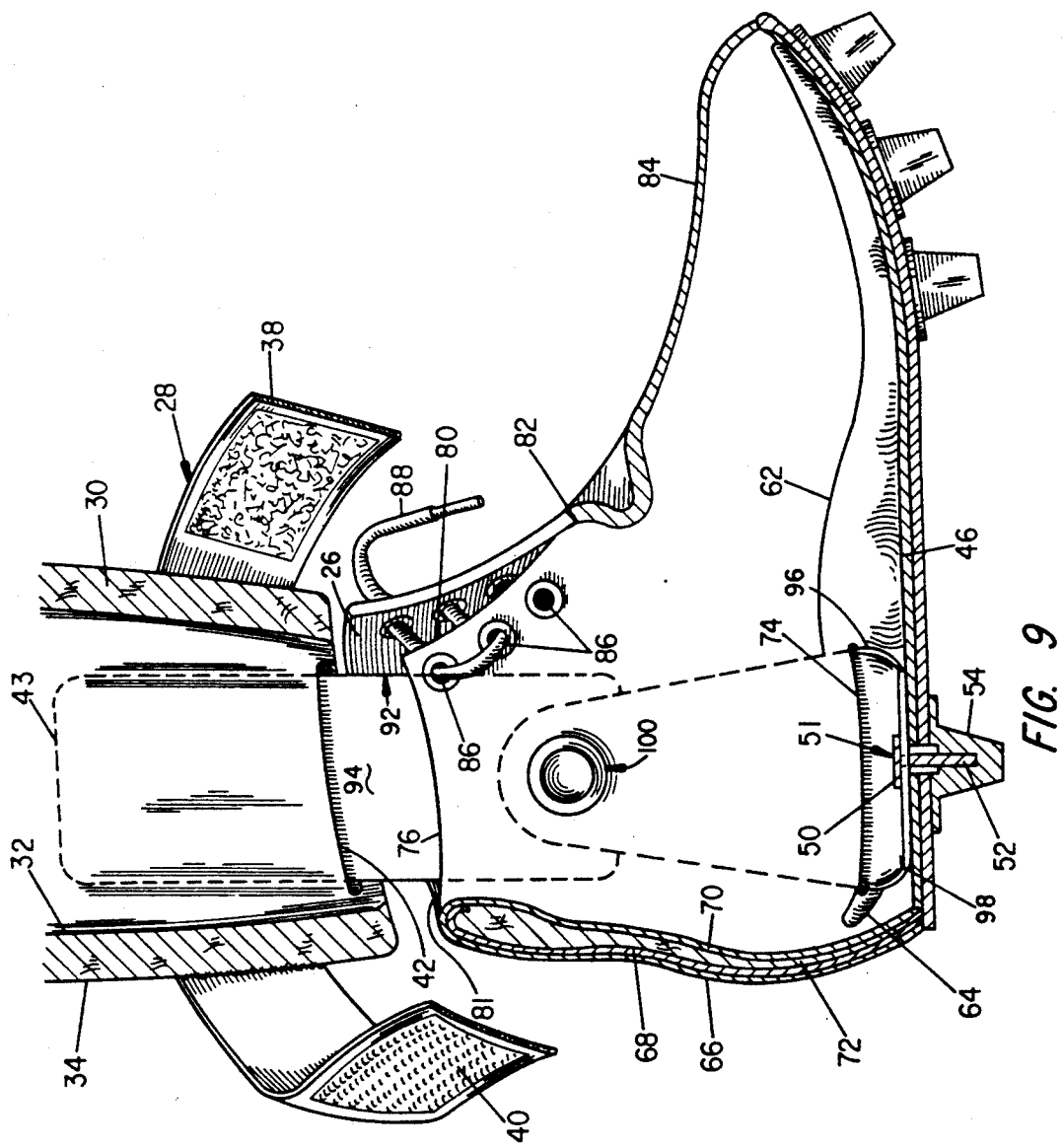

ATHLETIC FOOTWEAR WITH INTEGRAL ANKLE SUPPORT

BACKGROUND OF THE INVENTION

The present invention relates to athletic footwear and, in particular, to a brace and footwear adapted with the brace to resiliently restrain the foot against excessive ankle movement in predetermined axial directions, thereby preventing potential ankle injuries, yet permitting normal movement.

Numerous injuries are sustained annually by participants actively engaged in a variety of sports. Many of such injuries arise from insufficient support to the ankle by way of commercially available shoe constructions. That is, the footwear either provides no support to the ligaments, bone and cartilage structure of the ankle or insufficiently supports the ankle relative to the activity.

With the exception of downhill ski boots and rollerblade boots, essentially all shoes provide a soft-sided exterior shell. Included cushioning and liners protect the foot from abrasion with repeated contact with the walls. The cushioning otherwise does not particularly support the ankle structure or lower calf from undue forces of inversion/eversion, torsion or flexion. Such forces occur with normal foot movement or from unintended stress, such as placed on the ankle in contact sports.

Applicant is aware of various solutions which have been posed to the foregoing deficiencies. However, such solutions have only piecemeal addressed the involved problems, as opposed to taking an integrated approach.

Applicant is particularly aware of U.S. Pat. Nos. 260,069; 1,441,067; 1,549,382; 1,692,896; and 4,719,926 which show various brace assemblies that include multisectioned, metal parts. Portions of the braces are pivotally supported to articulate with respect to one another and the shoe. The braces, otherwise, are not fastened to the shoe. The metal braces are also susceptible to failure at the pivot joints and present problems of abrasion and structural fatigue (i.e. bending or fracture) from repeated flexion.

Another device of which Applicant is aware is shown in U.S. Pat. No. 4,621,648 which discloses a brace that separately mounts to the foot and includes straps that mount to the shoe, once the braced foot is inserted into the shoe. U.S. Pat. No. 4,821,743 discloses a shoe that contains formed pockets in the liner for receiving a resin formed ankle brace. The brace extends only the height of the shoe and is restrained only by the normal shoelaces etc.. U.S. Pat. No. 3,613,273 shows a cushioned collar for an externally supported brace of laminated construction. The braces of the latter reference also are intended to be mounted to only one surface of the leg and/or require specially formed shoes.

In contrast to the known art and commercially available shoes, Applicant believes a bilateral system including a pair of polymer braces or an integral brace, which are fastened or retained to the shoe and which are supported to the foot and the lower calf provides a preferable support system to control applied ankle stresses. Such a system also accommodates an after-market mounting to existing athletic shoes or shoes configured to accommodate a subsequent insertion of the brace system.

SUMMARY OF THE INVENTION

It is accordingly a primary object of the present invention to provide an ankle support system usable with specially formed footwear.

It is a further object to provide a system which mounts to or within athletic footwear to provide bilateral support in the region of the ankle and lower calf.

It is a further object of the invention to provide a system which accommodates normal healthy foot movement required by the intended activity, yet progressively limits or controls movement in predetermined axial directions which can produce injury.

It is a further object of the invention to limit certain axial movements via a resilient brace system constructed to resist predetermined, injury inducing axial movements.

It is a further object of the invention to provide footwear wherein each shoe includes a pair of vertical, cushioned polymer braces which are supported to the foot in the region of the ankle and lower calf.

It is a further object of the invention to provide footwear including cushioned liners containing pocket-parts or attachments to the liner which contain the brace to the liner and accommodate after-market mounting of the brace system.

It is a further object of the invention to provide footwear including a separately attached collar or upper calf restraint which receives and contains an upper end of each brace to the lower calf.

It is a further object of the invention to provide formed polymer braces which are shaped to align with the curvatures of the lower calf and ankle and include a portion which mounts beneath the heel or instep and which may removably attach to the shoe.

It is a further object of the invention to provide braces including apertures which accommodate the protruding ankle structure.

Various of the foregoing objects, advantages and distinctions of the invention are particularly obtained in preferred arrangements which are adaptable to athletic footwear of a court or cleated shoe construction. Such footwear particularly provides a pair of cavities or hemmed pockets which are formed in the linings or strap restraints otherwise secured to the lining of each shoe to receive a pair of brace members. Bent minor end portions of each brace mount beneath the heel and/or instep. Longer, major portions of each brace conformably extend along the inner and outer surfaces of the ankle and calf.

The braces extend approximately mid-height of the calf or approximately 10 inches. The braces are configured of a molded plastic or fiberglass composite tailored to particularly and progressively flex with increasing resistance, yet withstand disruptive forces to fibular calcaneal ligaments and the anterior talar fibular ligament. The latter ligament disrupts of approximately 200 newtons. The flexion properties of each brace are thus tailored to provide controlled brace flexion in certain predetermined axial directions.

For court shoes, the minor ends of each pair of braces are mounted in overlapped relation to one another, before being placed beneath and fastened to the sole. For cleated shoes, the minor ends are fastened in abutment to one another at the heel. Separate cushioned collars wrap about the lower calf and retain the brace ends which project from each shoe. Strap fasteners secured to the outer surfaces of each collar encircle the brace ends to restrain the braces and collar to the calf.

In another arrangement, a cushioned U-shaped brace, including relief apertures for the ankles, may mount about the leg and be restrained to the leg by the collar and/or the shoe via fasteners or straps.

In still another arrangement, a pair of hinged, polymer ankle braces are contemplated. The braces are retained to the shoe with fasteners and the calf with a cushioned collar.

Still other objects, advantages and distinctions of the invention will become more apparent from the following detailed description with respect to the appended drawings. To the extent various modifications and improvements have been considered thereto, they are described as appropriate. The description, however, is intended to be illustrative only of considered constructions or described modifications and improvements and should not be interpreted in strict limitation thereto. Rather, the invention should be interpreted within the scope of the following appended claims.

BRIEF DESCRIPTION OF THE DRAWINGS

FIG. 9 is an elevation of a pair of two-piece, hinged braces which is secured to a shoe and the calf in a fastener similar to the brace of FIG. 6.

DESCRIPTION OF THE PREFERRED EMBODIMENT

Figure 1:
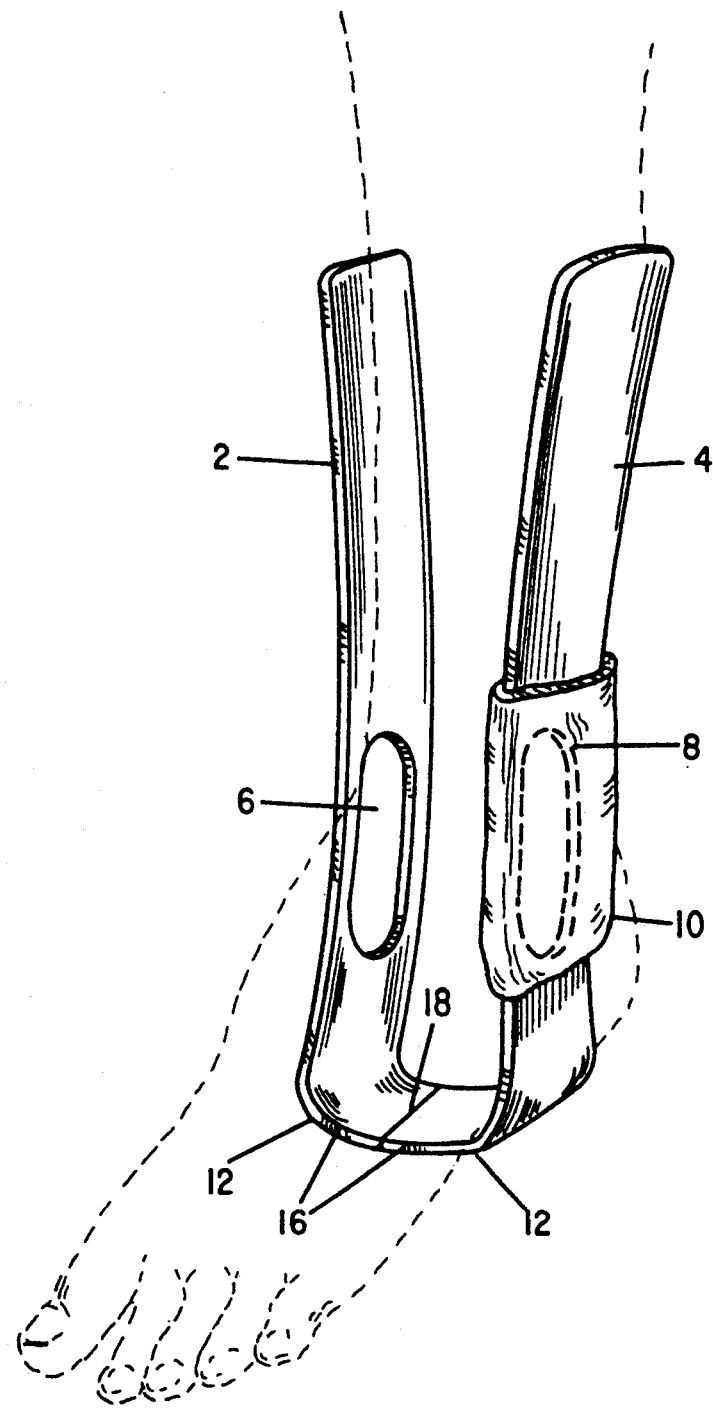
FIG. 1 is a perspective drawing showing the molded braces of the invention in mounted relation to the ankle and calf which is shown in phantom line.

Referring to FIG. 1, a perspective drawing is shown of a pair of braces 2,4 of the subject invention in mounted relation to the ankle and calf (shown in phantom). The braces 2,4 bilaterally support the ankle and calf from commonly experienced axial forces. These forces can be experienced as flexion, torsion, inversion, eversion, extension and rotation.

A pair of polymer braces 2 and 4 are particularly provided which exhibit predetermined flexion characteristics. The braces 2,4 are constructed to flex with progressively increasing resistance in certain axial directions. The braces 2 and 4 respectively mount along the instep and outside surfaces of the ankle and extend upward approximately 10 to 12 inches along the sides of the calf to stabilize the shoe and ankle relative to the lower regions of the tibia.

Each brace is approximately 2 to 4 inches wide and includes an appropriately configured aperture 6 and 8. The apertures 6,8 permit the protrusion of the ankle structure through the respective braces 2,4, yet accommodate normal foot and ankle movement without causing abrasion. The specific shape of each aperture 6,8 is formed to accommodate the differing shapes and positioning of the opposite sides of the bone and cartilage structure at the ankle.

A cushioned sleeve 10 may be separately mounted about each brace 2,4 in the region of each aperture 6,8 or along a substantial portion of the length of each brace. The particular positioning and extent of the cushioning 10 depends upon the intended mounting of the braces 2,4. Where the braces are purchased for aftermarket modification of a pair of shoes, such as shown in FIG. 1, the cushioning 10 is normally provided. For other constructions described below, the cushioning 10 may be deleted in preference to alternative mounting configurations wherein the cushioning is integral to the shoe.

Figure 8:
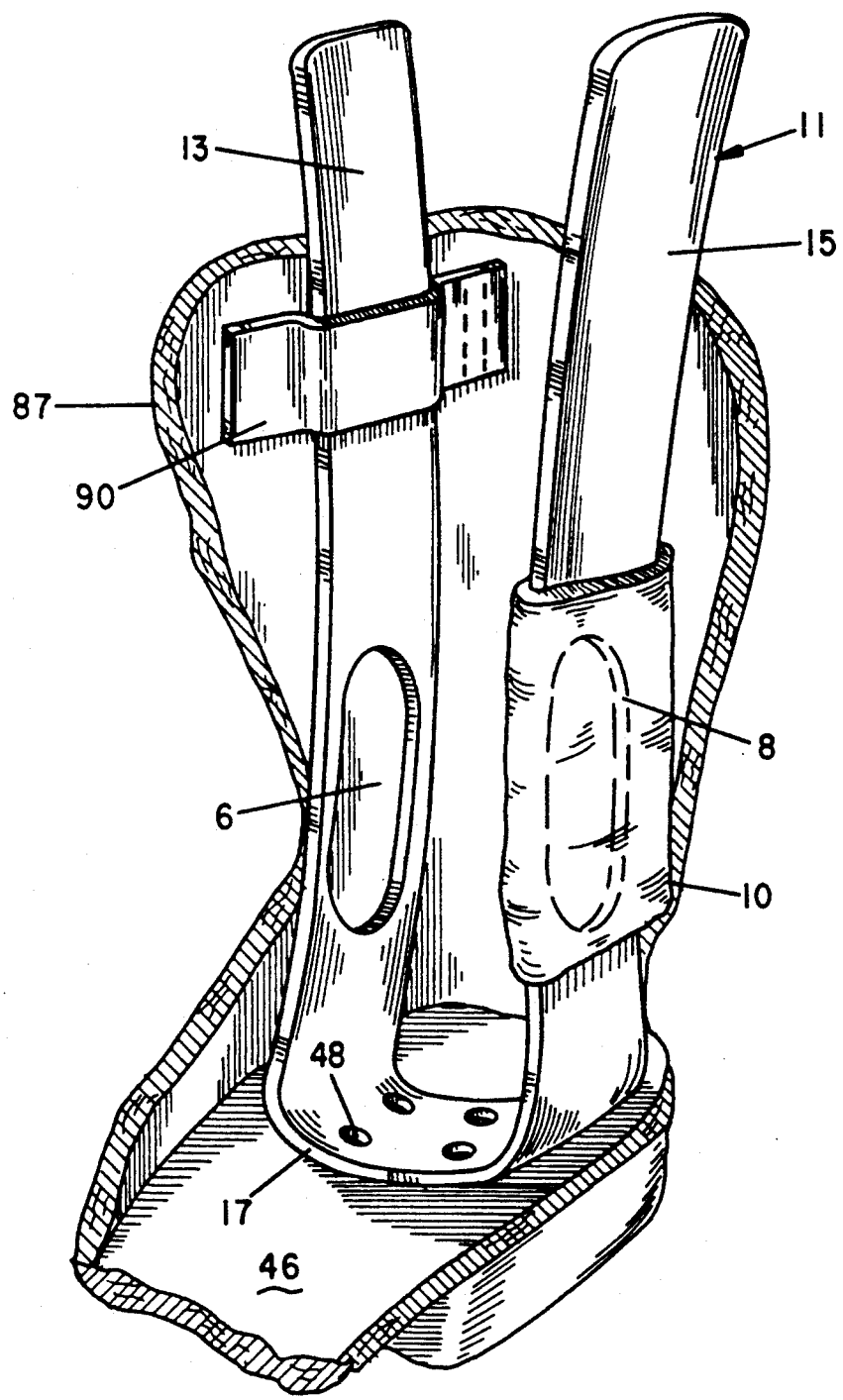
FIG. 8 is a perspective drawing of a cushioned unitary brace, with portions of the shoe shown in cutaway, which mounts about the ankle and which is fastened not shown to the shoe with straps and through fasteners.

FIG. 8 shows a U-shaped unitary brace 11 which includes integral upright portions 13 and 15 and a joining cross-piece or bridge 17. Appropriate apertures 6,8 and cushioning 10 are provided as necessary. Such a brace 11 can be mounted about each foot and ankle, prior to inserting each foot into a shoe and may be used with or without the collar 28 discussed below in regard to FIG. 5. As depicted the brace 11 is fastened to the sole 46 and liner 87. Alternatively, the brace 11 can be integrated into the shoe.

Returning attention to FIG. 1, each brace 2,4 includes a lower or minor bent end portion 12 which is radiused to mount beneath the heel. The radius of the bend at each portion 12 is established to not only direct the brace about the foot, but also to maintain the brace in close proximity to the ankle and calf via appropriate lateral adjustment, before attaching each brace to the shoe. The flattened portion 16 of each end 12 may mount in overlapped relation to one another, such as shown in the court shoe construction 21 of FIGS. 2 and 4. Alternatively, the extreme end edges 18 of each brace can mount in abutment to one another as depicted, or as also shown in a cleated shoe 22 at FIGS. 3 and 7.

Each brace 2,4 is formed of a molded plastic or resin based polymer. Polymers which exhibit desired shape retention and flexion resistant properties are orthoplast, alloplast, polypropylene, kevlar etc.. Various fibrous composites, such as fiberglass may also be used. Woven filaments or stranded materials may be added to directionally stabilize the brace either vertically, radially or otherwise, for the typically anticipated forces.

By varying the composition and/or thickness of the brace material, the ankle of the wearer is stabilized against undue inversion/eversion, flexion, torsion, extension and rotation which can result from many sporting activities. Normal foot movement is otherwise not compromised, since the ball of the foot and toes are free to perform in uninhibited relation to the shoe and accommodate necessary foot movement for the activity. The composition of the brace and rigidity can be selectively tailored to accommodate certain types of sports activities and preferred, healthy foot movements.

Figure 3:
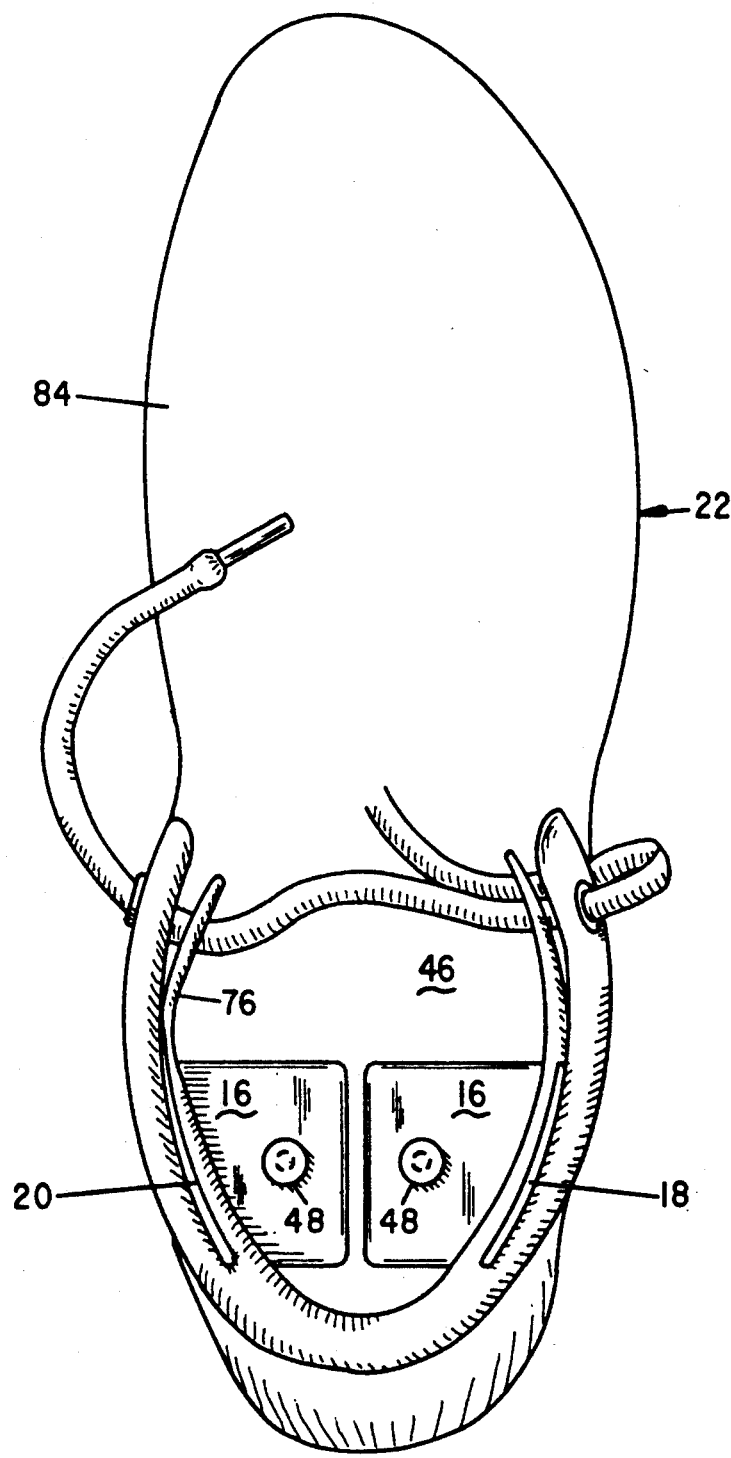
FIG. 3 is a generalized top plan view of a cleated shoe containing the brace system of the invention.
Figures 4, 7:
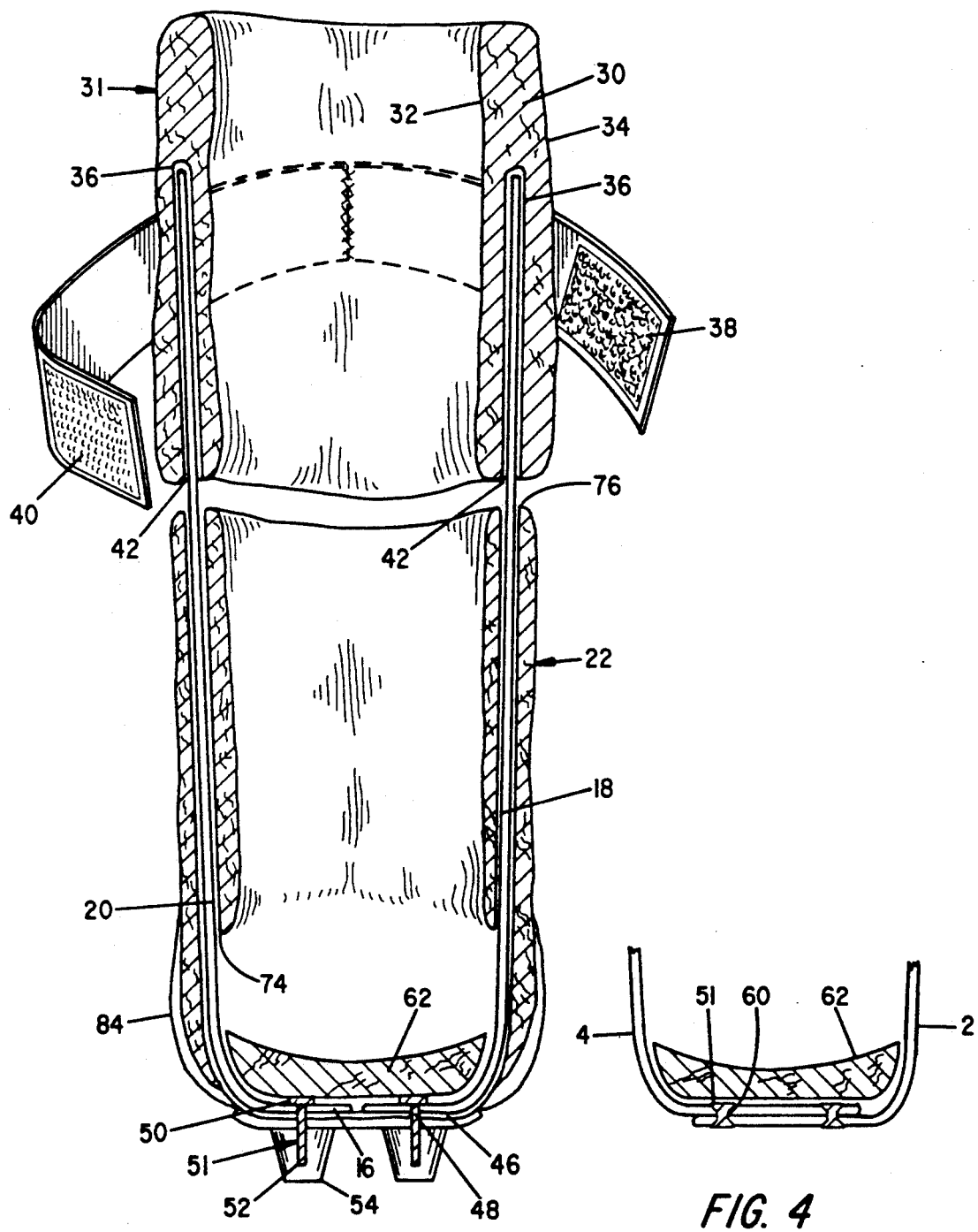
FIG. 4 is a detailed elevation drawing of the overlapped mounting of the braces for the court shoe construction of FIG. 2.
FIG. 7 is an elevation drawing, shown in cross-section and looking to the back, of the shoe of FIG. 3.
Figure 5:
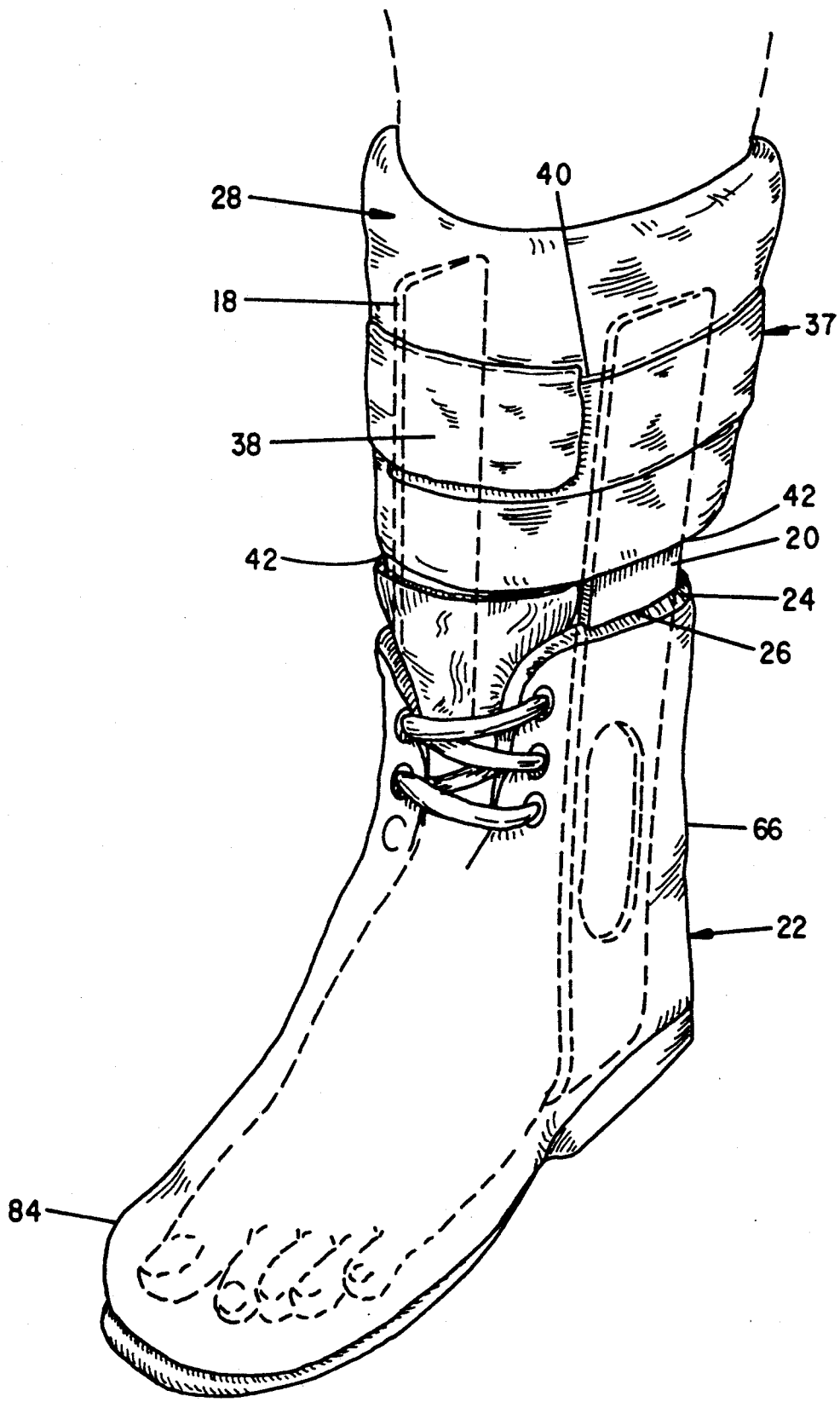
FIG. 5 is a perspective drawing of the shoe of FIG. 3 mounted to the foot and lower calf.
Figure 6:
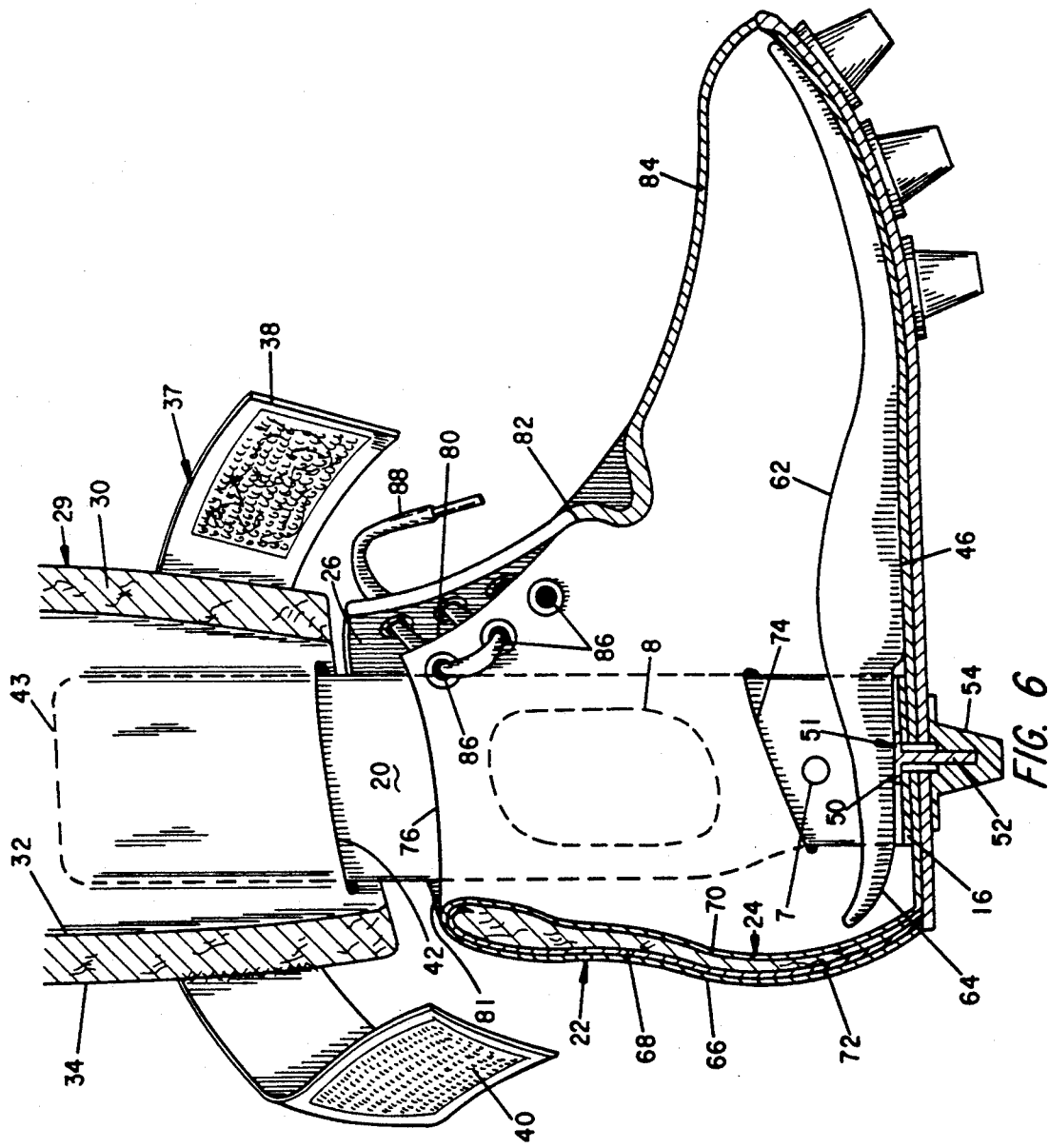
FIG. 6 is a partial perspective drawing shown in cutaway and cross section of the shoe of FIG. 3.

Referring to FIG. 5 a drawing is shown of a pair of braces 18, 20 which are incorporated into the cleated athletic shoe 22 which might be used when participating in football, soccer or other field sports. FIGS. 3, 6 and 7 show other views of the shoe 22. As depicted, a pair of braces 18, 20 are secured adjacent the heel and instep portion to the sole of the shoe 22. The braces 18, 20 project from the shoe 22 at a stitched or hemmed opening 26 to a channelway formed in a cushioned, inner lining 24.

The projecting ends of each brace 18,20 are, in turn, received at a separate cuff or collar support 28 which contains a separate cushioning material. Various resilient materials, such as foams or neoprene, or layered assemblies containing thinner, slippery, high durability materials are typically contained within the collar 28. Similar materials may be used beneath the shoe lining 24. FIG. 6 shows an alternative collar arrangement 29, similar to FIG. 5, but wherein a foam 30 is mounted between inner and outer coverpieces 32 and 34, which can be cloth or skinned over portions of the foam. FIG. 7 shows still another collar arrangement 31 wherein the upper brace ends are mounted in channels 3,6 formed between facing and backing pieces of the cushioning 30.

A relatively dense, semi-compressible or resilient filler material is particularly desired to cushion the calf from the relatively stiff brace members 18,20. Preferably, the cushioning material is slippery relative to the material from which the braces 18,20 are constructed. Upon enveloping the exposed ends of the braces, the collar 28 protects the calf and the skin from possible chaffing or abrasion. The outer coverpiece of the collar 28 may be made of neoprene or leather, while the inner coverpiece can be made of a tightly woven nylon fabric or kevlar. Consideration must also be given to the capabilities and configuration of the selected cushioning and covering materials to withstand the effects of perspiration, to wick away accumulating perspiration, to prevent chaffing, and to permit cleaning, among other considerations.

Secured to the outer cover of the collar 28 is a relatively wide strap 37 which contains end fasteners 38, 40. VELCRO fasteners are preferred. Straps which include mating buckle assemblies may also be used. The fasteners 38,40 must also accommodate a wide range of adjustment relative to the calf, permit cleaning and maintain an established mounting tension with normal use. Such goals are presently believed to be best achieved with a VELCRO fastened strap.

A pair of slots 42, which are also present in the collars 29 and 31, are formed adjacent the bottom peripheral edges of the collar 28 to receive the upper ends of the braces 18,20. The slots 42 align with the respective apertures 74 in the shoe 22 to receive the braces, either in a temporary or semi-permanent mounting. In the later regard, removable fasteners (not shown) might be used to secure the upper end of the braces to the collar 28. Such an arrangement retains each collar 28 to the braces 18,20 and to the shoe 22 to prevent inadvertent separation and loss of the collar 28.

Re-directing attention to FIG. 7 and also to FIG. 3, FIG. 7 shows a rear view of the mounting of the braces 18,20 to the cleated shoe 22. The minor end 16 of each brace 18,20 is supported from an inner sole 46 in flat engagement with the sole 46. One or more apertures 48 formed in each brace align with a flattened head 50 of a related fastener 51. A stem piece 52 particularly mounts through the aperture 48 and a bored hole formed through the inner sole 46 and heel of the shoe.

A mating threaded fastener portion mounted to the outer sole of the shoe cooperates to draw the braces 18,20 into engagement with the inner sole 46 and bind the braces to the shoe. The mating fastener may comprise a portion of a cleat 54 which includes a threaded bore that receives the stem of the fastener 51. Various other draw fasteners might also be appropriately substituted, provided a relatively flush mounting is obtained at each exposed inner surface of the sole. Countersunk apertures 60 can also be provided to recess the fastener ends into the upper surface of the brace, reference FIG. 4. Each brace, otherwise, is similarly secured to each shoe, once the necessary lateral spacing is determined for the athlete.

Figure 2:
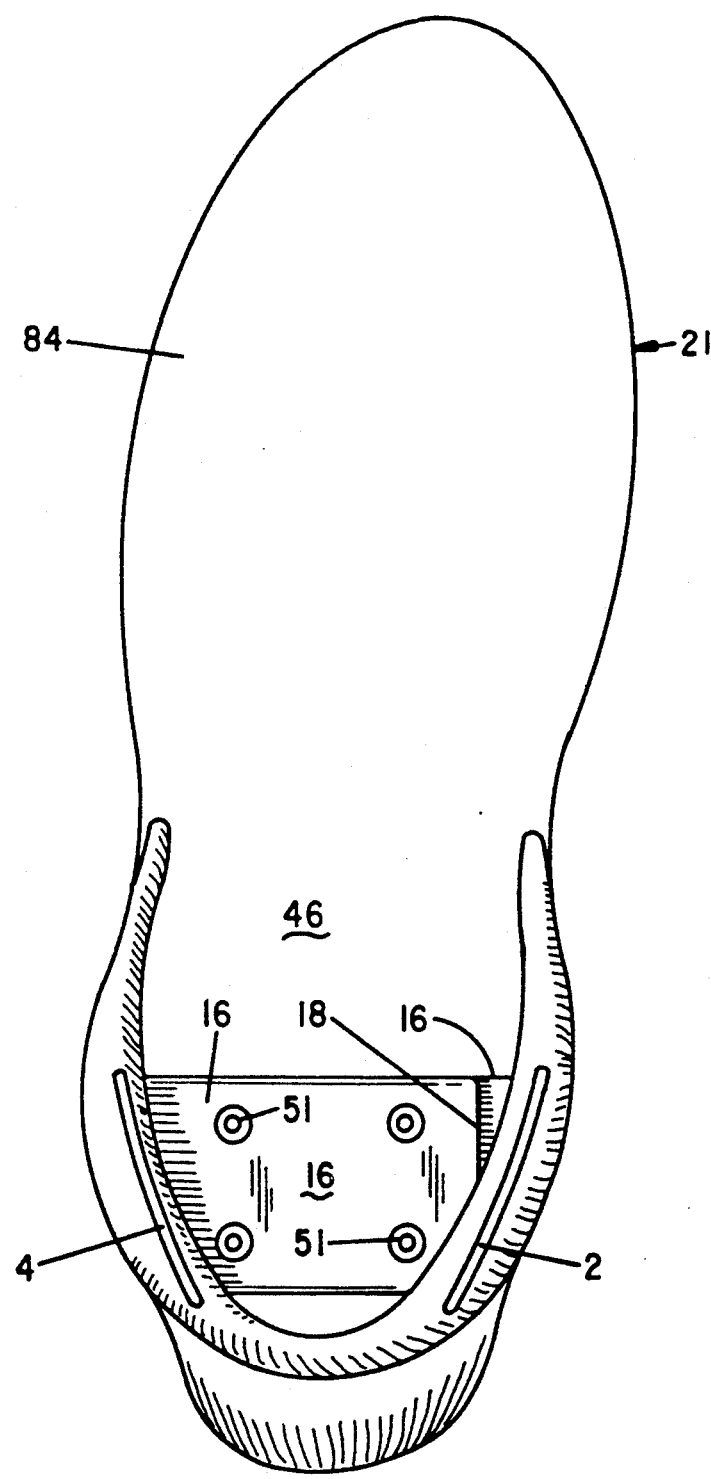
FIG. 2 is a generalized top plan view of a court shoe containing the brace system of the invention.

From FIG. 2 and for the court shoes 21, it is to be appreciated that the minor brace ends 16 are typically mounted in overlapped engagement to one another. The fasteners 51 extend through holes formed in both braces and the shoe as described above. Countersunk holes 60 are particularly employed in this arrangement. Due to the typical flexibility of most court shoes, more fasteners may be required than for cleated shoes. A unitary brace construction, reference FIG. 8, may also prove to be more beneficial in some circumstances.

Once the braces are fastened to the shoe 22, a sole pad 62 is mounted over the braces 18,20 to line the shoe. To assure that the wearer does not experience discomfort relative to the underlying brace assembly, the pad 62 can be constructed from a molded plastic, elastomer or polymer. A cut-out or recessed channelway 64 is formed into the pad 62 to align with the fastened braces. Otherwise the sides of the pad extend partially along the inner periphery of the shoe and are tapered to provide a slight cupping but which does not chafe the foot.

Returning attention to FIGS. 6 and 3, enlarged brace access slots 76 are provided to the channelway formed between the apertures 76 and 74 to facilitate after-market mounting of the braces 18,20. After market mounting permits modification and stabilization of a shoe, after ankle injury, to facilitate treatment or rehabilitation or to minimize the likelihood of future injury. A flap 80 at the inner liner 70 is particularly defined between a stitch point 81 at the aft end of the shoe and a stitch point 82 adjacent the aft edge of the vamp 84. Intermediate the stitch point 82 and upper edge of the shoe, eyelets 86 are provided in the liner 70 and through which tie fasteners 88 secure the liner 70 to the shoe 22, as well as the outer overlapping shoe walls to each other. Alternatively, VELCRO fasteners can be provided between the liner and the inner surface of the outer cover or shell 66, which for cleated footwear typically comprises leather. The intent is to provide a wide acceptance aperture 76 to permit the mounting of the bent minor end of each brace 18, 20, when inserted into the shoe 22 after original manufacture.

The braces otherwise mount between the shell 66 and a fibrous inner layer 68 or in the space containing the cushioning 72, between the layer 68 and a layer 70. Depending upon whether the brace is added during or after manufacture of the shoe, the size of the lower slot 74 can also be varied. Larger slots would be provided for after market mounting. Additional layers or portions of the liner material may also be formed into the shoe, reference FIG. 7, to present a slippery channelway for the braces 18,20 and such that both sides of the braces are cushioned.

In lieu of the flap 80, the layer 70 can be provided with a number of VELCRO straps 90 secured to the layer 70 in a fashion similar to that shown at FIG. 8. For such a mounting, the straps 90 are cinched over the later added braces which preferably would contain separately attached cushioning 10.

Suitably sized apertures or cut-outs 6,8, otherwise, are formed along the longitudinal length of each brace 18,20 to accommodate the protruding ankle bone structure. The shape and positioning of the cut-outs may be varied as necessary to the particular individual. Most typically, the aperture 6 on the instep side of the ankle is more elongated than the aperture 8. This is not only due to the shape of the bone structure but also to accommodate the greater range of required movement of the inner ankle structure. The peripheral edges of the apertures are typically rounded and smooth. The hole size is also adjusted to minimize chaffing. Other apertures 7 may also be included at strategic points along each brace to provide controlled flexion of the braces.

Although the preferred construction of the invention contemplates footwear including an inner liner which constrains the brace members thereto at the time of manufacture, it is to be appreciated that the braces can be added at a later time, as discussed at FIGS. 3, 6 and 7. In this regard, another possible after-market brace system is shown at FIG. 8. This system provides an integral, U-shaped brace 11 which includes padded sleeves 10. Alternatively, the brace 11 might be dipped or otherwise coated with a suitable elastomer.

Straps 90 secured to the inner liner 87 of a pre-modified shoe secure the brace 11 to the shoe. Fasteners, such as the fasteners 51, preferably secure the bridge portion 17 of the brace 11 to the sole 46 at apertures 48 provided in the brace 11. A cushioned, stocking restraint might alternatively be used to restrain the brace 11 to the foot without attachment to the sole. The upper ends of the uprights 13,15 of the brace 11, as with the braces 2,4; 18,20, are supported to the calf with the earlier described cushioned collar 28.

Still another alternative brace system is shown at FIG. 9. One of a pair of two-piece, hinged braces 92 is particularly depicted in mounted relation to a shoe in a fashion similar to the mounting shown in FIG. 6. Although only one brace 92 is shown, each of the braces 92 is secured to the calf with the collar 28 and to the shoe with one or more fasteners 51.

The brace 92 is constructed of a polymer material, such as previously described, and provides upper and lower portions 94 and 96. The upper portion 94 exhibits an essentially planar configuration and mounts to the collar 28. The lower portion 96 includes a bent minor end 98 which is secured to the shoe, after exiting an aperture 74 in the liner. A pivot fastener 100, otherwise, retains the portions 94 and 96 to one another and is supported inside the cushioned liner. Either a separate fastener 100 can be used or mating fastener portions might be formed into the portions 94, 96 which suitably mount to each other to withstand the encountered stresses. At present, a low profile, permanent rivet type fastener is contemplated.

The invention has principally been described with respect to a number of considered alternative constructions, and various modifications and improvements thereto. It is to be appreciated, however, that still other modifications and improvements may suggest themselves to those skilled in the art. Accordingly, the following claims should be interpreted to include all those equivalent embodiments within the spirit and scope thereof.

What is claimed is:

1. Ankle support apparatus comprising:
   (a) a shoe having an outer shell and a liner means secured to an inner surface of said shell for cushioning a foot surrounded by said shell and including means for defining a plurality of open-ended channelways;
   (b) first and second polymer braces, wherein each brace includes a minor arm portion which mounts adjacent a heel region of said shoe, a major arm portion which extends from said minor arm portion, and means for accomodating an ankle protrusion, and wherein a portion each of said first and second braces projects from one of said channelways;
   (c) means for fastening said first and second braces to said shoe; and
   (d) collar means for restraining said first and second braces to the calf and including a covered cushion having means for supporting the projecting portions of said first and second braces to said collar means, and fastener means for binding said collar means and the projecting portions of said first and second braces to the calf.

2. Apparatus as set forth in claim 1 wherein said shoe further comprises a court shoe and the minor arm portion of each of said first and second braces is mounted in overlying relation to the other.

3. Apparatus as set forth in claim 2 wherein said shoe includes a sole pad having a recess and wherein said overlapped braces mount within said recess.

4. Apparatus as set forth in claim 1 wherein the brace fastening means comprises a plurality of screw fasteners which mount through a plurality of apertures in the minor arms of said first and second braces.

5. Apparatus as set forth in claim 4 wherein said apertures are countersunk to receive a head portion of said screw fasteners.

6. Apparatus as set forth in claim 1 wherein said shoe further comprises a cleat portion and a distal end of the minor arm of each of said first and second braces abut one another and are fastened to said shoe with a plurality of fasteners which cooperate with said cleat portion and which contains a mating fastener portion.

7. Apparatus as set forth in claim 1 wherein said collar means includes first and second channelways for containing the projecting portions of each of the first and second braces.

8. Apparatus as set forth in claim 7 wherein each of the channelways of said shoe and said collar are comprised of an abrasion resistant and slippery material relative to said first and second braces.

9. Apparatus as set forth in claim 1 wherein the ankle protrusion means comprises respective first and second apertures in said first and second braces.

10. Apparatus as set forth in claim 9 wherein each of said first and second braces is coated with an elastomer.

11. Apparatus as set forth in claim 1 wherein each of said first and second braces are formed from a fiber containing resin and exhibit a width in the range of $1\frac{1}{2}$ to 4 inches and a heighth between 6 and 12 inches.

12. Apparatus as set forth in claim 11 wherein selected regions of said fibers are wound in different predetermined axial orientations such that preferential flexion characteristics are imparted to each of said first and second braces.

13. Apparatus as set forth in claim 11 wherein each of the first and second braces include a plurality of apertures whereby the axial flexion properties of the first and second braces are tailored.

14. Apparatus as set forth in claim 1 including a stocking having a pair of tubular channelways wherein said major ends of said first and second braces are restrained.

15. Apparatus as set forth in claim 1 including strap means for restraining each of said first and second braces to the liner means of said shoe.

16. Apparatus as set forth in claim 1 wherein said liner means includes respective first and second flap portions at ones of said channelways and means for securing said first and second flap portions to the outer shell upon admitting said first and second braces to the channelways.

17. Ankle support apparatus comprising:
(a) a shoe having an outer shell and liner means secured to said an inner surface of said shell and including a plurality of openings for cushioning a foot surrounded by said shell;
(b) polymer brace means formed to include a heel portion which mounts adjacent a heel region of said shoe, first and second arms which extend from said heel portion, and means for receiving an ankle protrusion, and wherein portions of each of said first and second arms are cushioned by said liner means and project from one of said openings;
(c) means for retaining said heel portion to said shoe; and
(d) collar means including a cushion portion for supporting ends of said first and second arms which project from said openings and fastener means for binding said collar means and said brace means to the calf.

18. Apparatus as set forth in claim 17 wherein the protrusion receiving means comprises respective first and second openings in said first and second arms.

19. Ankle support apparatus comprising:
(a) a shoe having an outer shell and liner means secured to an inner surface of said shell for cushioning a foot surrounded by said shell and for defining a plurality of open-ended channelways;
(b) polymer brace means including a heel portion which mounts adjacent a heel region of the shoe, first and second arms which extend from said heel portion, and means for receiving an ankle protrusion, and wherein a portion of each of said first and second arms project from one of said channelways; and
(c) collar means for restraining said first and second arms to the calf and including a covered cushion portion having means for supporting said first and second arms to said collar means, and fastener means for binding said collar means and said first and second arms to the calf.

* * * * *